United States Patent [19]
Dakubu

[11] Patent Number: 5,124,268
[45] Date of Patent: Jun. 23, 1992

[54] METHOD OF DETERMINING A BIOLOGICAL SUBSTANCE INVOLVING LABELLING WITH A METAL CHELATE

[75] Inventor: Salifu Dakubu, Winchester, Mass.

[73] Assignee: Roger P. Ekins, London, England

[21] Appl. No.: 340,414

[22] PCT Filed: Sep. 22, 1987

[86] PCT No.: PCT/GB87/00663
§ 371 Date: Apr. 13, 1989
§ 102(e) Date: Apr. 13, 1989

[87] PCT Pub. No.: WO88/02489
PCT Pub. Date: Apr. 7, 1988

[30] Foreign Application Priority Data
Sep. 23, 1986 [GB] United Kingdom ............... 8622855

[51] Int. Cl.$^5$ .................................. G01N 33/542
[52] U.S. Cl. .................................................. 436/537
[58] Field of Search ....................................... 436/537

[56] References Cited
FOREIGN PATENT DOCUMENTS
0064484 11/1982 European Pat. Off. .
8601604 3/1986 World Int. Prop. O. .

*Primary Examiner*—Robert A. Wax
*Assistant Examiner*—Fred Tsung
*Attorney, Agent, or Firm*—Dann, Dorfman, Herrell and Skillman

[57] ABSTRACT

A biological substance is determined with the use of a marker comprising a lanthanide or other metal ion coupled to the biological substance by means of chelate-forming compound. The chelate complex is dissociated by reduction of the ambient pH to a sufficiently low level to liberate the metal ion and the metal ion is then chelated with a separate chelating chromophore with an increase in the pH to a value closer to the optimum for determination of the metal-chelated chromophore by fluorescence spectroscopy, luminometry, colourometry or the like.

23 Claims, 6 Drawing Sheets

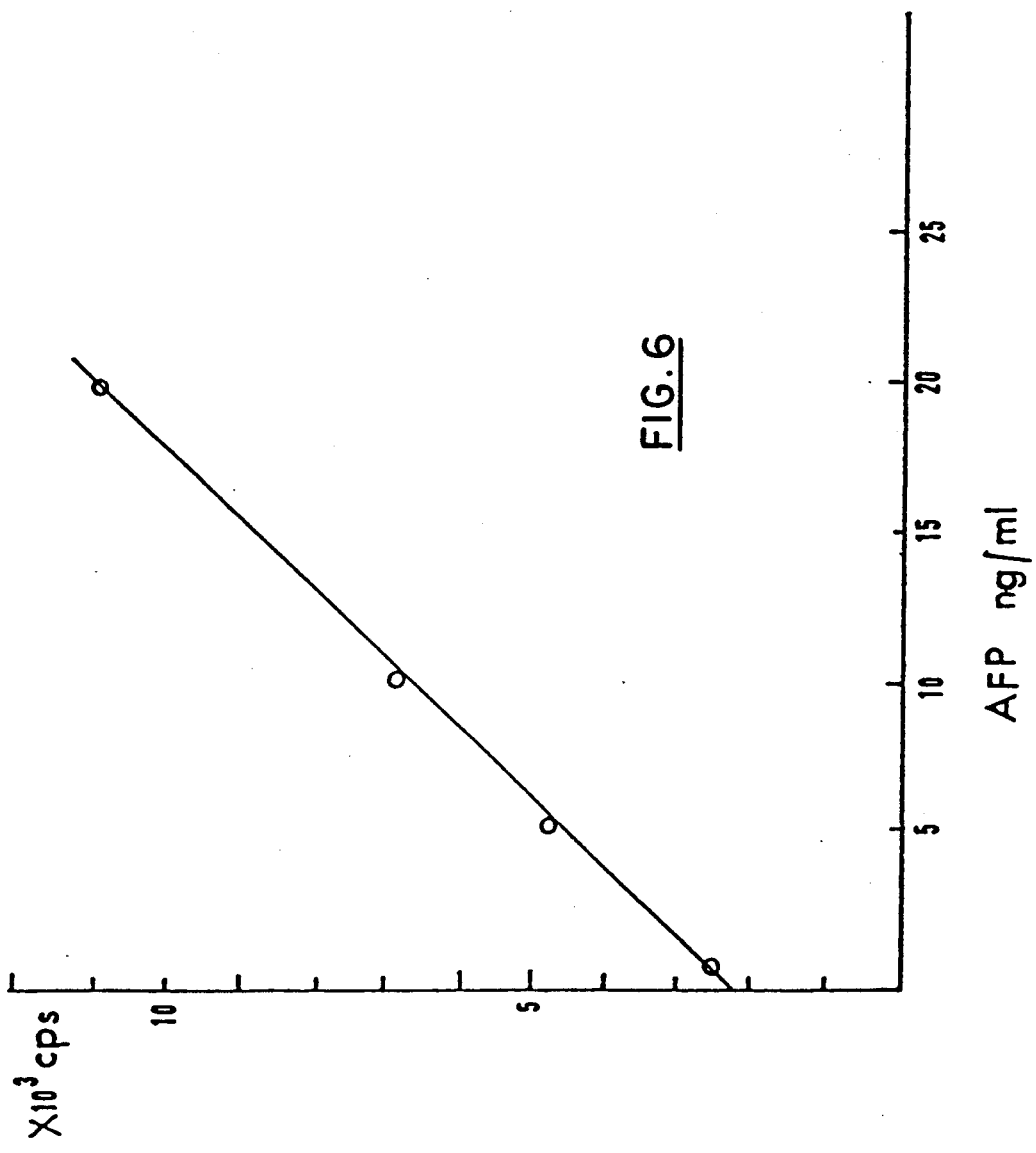

METHOD OF DETERMINING A BIOLOGICAL SUBSTANCE INVOLVING LABELLING WITH A METAL CHELATE

TECHNICAL FIELD

The present invention relates to a method of determining a biological substance involving labelling with a metal chelate. The determination being performed for example by fluorescence spectroscopy, luminometry or colourometry.

BACKGROUND ART

Methods are already known for the fluorescence spectroscopic determination of a biological substance provided with a marker consisting of a lanthanide chelate complex, formed of a lanthanide metal ion such as a europium ion or terbium ion coupled to the substance via a chelate-forming compound such as ethylene diamine tetraacetic acid (EDTA) or an analogue thereof, by excitation by a short radiation pulse and detection of the fluorescence of the marker when the fluorescence from any noise source has substantially ceased. These methods have application in time-resolved fluorometric assays using labelled tracer molecules such as labelled antigens or antibodies or nucleic acid probes.

U.S. Pat. No. 4,565,790 and European Patent 0,064,484 disclose an improvement in such a process in which, before the determination is carried out, a solution of low pH, which suitably brings the pH to 3.5 or below and contains a detergent and a β-diketone, is added to dissociate the lanthanide ion from the chelate complex and to transfer the dissociated lanthanide ion into a fluorescent form, whereupon the determination is performed in the solution.

As described in those patents the solution added to reduce the pH necessarily contains a detergent and the determination of the fluorescence is necessarily carried out at the low pH, said to be suitably 3.5 or less. Also, the only disclosure of the addition of β-diketone is as part of the low pH solution. The present invention seeks, inter alia, to improve that process.

DISCLOSURE OF THE INVENTION

We have found that none of the features mentioned in the preceding paragraph is essential to the successful determination of the fluorescence, and better results can be obtained more rapidly by operation in a different manner.

According to a first aspect of the present invention a method for the fluorescence spectroscopic determination of a biological substance provided with a marker consisting of a lanthanide chelate complex formed of a lanthanide metal ion coupled to the substance via a chelate-forming compound comprises adding to the chelate complex a solution which reduces the pH to a level at which the lanthanide metal ion becomes dissociated from the chelate complex and subsequently adding to the resulting solution a further solution which increases the pH to a level at which a complex formed between the dissociated lanthanide metal and a chelating chromophore incorporated in the solution is closer to its fluorescence peak for optimum sensitivity. The optimum concentration of the chelating chromophore employed is determined by the pH at which fluorescence measurement is made.

A more general aspect of this invention is the case where a metal ion, not necessarily a lanthanide metal ion, is carried on one chelate through a biochemical reaction to link with a biological substance to be determined and is then, for measurement purposes, released by dissociation and taken up into an appropriately formulated chelating chromophore for measurement by fluorimetry, luminometry or colourometry. Such an approach allows users the freedom to choose the best chelate for conjugation with the biological substance to be determined and with the tracer metal quite independently of the nature of the chelating chromophore used in the measurement step and independently of the optimum conditions for its use. It also does not require derivativization for attachment of the chelating chromophore of choice.

According to a further aspect of the present invention, therefore, there is provided a process for the determination of a biological substance comprising providing the substance with a marker consisting of a chelate complex composed of (i) a metal ion capable of being detected in conjunction with a chelating chromophore and (ii) a first chelate-forming compound capable of coupling the metal ion to the biological substance, isolating the substance with attached marker free from any content of the metal ion in uncoupled form, dissociating the chelate complex to liberate the metal ion substantially completely by reduction of the ambient pH, forming a different complex between the liberated metal ion and an added second chelate-forming compound capable of operating as a chelating chromophore for the metal ion by raising the ambient pH to a level appropriate for detection of the resulting metal-chelated chromophore, and determining the metal-chelated chromophore, for example by fluorescence spectroscopy, luminometry or colourometry, as a measure of the biological substance.

The present invention is based partly on the discovery that the contacting of a chelating chromophore (B) with a pre-existing metal chelate MX (metal—e.g. lanthanide—M+ chelating agent X to which the biological substance is attached) causes the chelating chromophore to oust the previous chelating agent and form a new binary chelate $MB_n$ (which may contain one or more, e.g. three, units of B, the number of units being represented by n) rather than a ternary chelate of the form MXB. The overall reaction can be expressed in terms of the following equilibrium:

$$MX + nB \rightleftharpoons MB_n + X$$

(where n is an integer), but the mechanism of the reaction is believed to involve the relatively slow preliminary dissociation of the initial chelate MX and then the relatively rapid formation of the new chelate $MB_n$. The rate-determining dissociation step has been found to be facilitated by a low pH, whereas the chelate-forming step is less pH dependent. At a pH of about 1.7 (say 1.5–2.0) metal M is essentially fully dissociated from the chelating agent X and is ready to form a chelate with the chromophore B. Thus if the chelate is initially subjected to a low pH and the chromophore added, the pH can then be raised again without significantly affecting the rapid rate, a matter of minutes, at which the final equilibrium between the initial chelate (MX) and final chelate ($MB_n$) is achieved, whereas if the chromophore (B) and initial chelate (MX) are simply contacted at higher pH, for example 5, 6, 8 or more, the rate at which equilibrium is achieved in the formation of the new chelate (MB$_n$) is very slow indeed, a matter of many hours if not days.

A detergent plays no role in the dissociation of the initial chelate, contrary to the suggestion in U.S. Pat. No. 4,565,790 and its presence or absence will not influence the rate of formation of the final equilibrium. Its only role, if it has one at all, is to assist in solubilising the chelating chromophore (B). Such a function may be of some importance in the case of β-diketone as the chelating chromophore, but it is not usually necessary in the case of other chromophores. A detergent is thus not an essential component of the present invention and it may be omitted.

The present invention is also based in part on the realisation that the optimum pH at which fluorescence of a metal (M) chelate (MB$_n$) with a chelating chromophore (B) is measured is not as a general rule a very low pH of 3.5 or less. Greater sensitivity and greater stability of signal can be achieved when using higher pHs of 5, 6, 8 or even 12 in appropriate cases depending on the identity of the chelate MB$_n$.

Thus the present invention is characterized not simply by a reduction in pH prior to determination of the fluorescence—as is characteristic of the process disclosed in U.S. Pat. No. 4,565,790—but by a reduction in pH followed by an increase in pH prior to the determination. This two-step pH change has not previously been proposed and yet is able to lead to marked improvements in speed and sensitivity of determination.

The level to which the pH is reduced by the addition of the first solution should be substantially below 7.0 because increasing the acidity of the solution increases the rate at which the lanthanide or other metal ion dissociates from the initial chelate complex. This may be because the increasing concentration of H$_3$O$^+$ ions competes more effectively with the lanthanide or other metal ions held in the chelate complex or because the chelate-forming compound is itself protonisable, as with polycarboxylic acids such as EDTA and its analogues. The optimum level, beyond which a further reduction in pH level brings no further benefits by way of increasing rate of dissociation and hence no quicker completion of the dissociation step, is dependent on the chelate-forming compound used to form the initial chelate complex with the lanthanide or other metal and the substance being determined. For most chelate-forming compounds the optimum pH is below 3.0 and it may be as low as 1.5-2.0, for example 1.7. However, pH levels which are above the optimum may be used in the practice of the invention, although the dissociation will in such cases be completed more slowly. Thus pHs up to 3.5, 4.0 or even more are not excluded. The reduction in pH may be achieved by the use of an appropriately buffered solution, using for example tris/HCl or tris/acetate buffers, or simply by addition of a calculated amount of strong acid such as hydrochloric acid.

The level to which the pH is raised again by means of the further solution should be one at which the chelate formed between the dissociated lanthanide or other metal ion and the chelating chromophore is fluorescent and will preferably be as close as possible to the optimum pH for the chelate. This optimum pH will usually be already known for known chelating chromophores but it can in any event be determined by performing trials at different pH levels and comparing the results. The rise in pH can be achieved by adding an appropriate buffer in an appropriate amount to increase the pH to a level which usually falls within the range 3 to 12, depending on the nature of the chelating chromophore, β-NTA for example giving optimum results at pH 5 and many other chromophores such as pyridoxamine, p-aminosalicylic acid, morin, hydroxykynurenine, and dipicolinic acid giving optimum results at pH levels of 8-12. By taking the pH back to the optimum level it is possible to measure the fluorescence much more quickly than if the pH remains at a low level, for example about 10 minutes instead of 24 hours. There is also greater sensitivity because the maximum concentration is higher. Reference is made to the paper entitled "The fluorometric determination of europium ion concentration as used in time-resolved fluoro immunoassay" by S. Dakubu and R. P. Ekins in Analytical Biochemistry, 144, 20-26 (1985), in this context.

The chelating chromophore can be a β-diketone, preferably a diaryl- or fluoroalkylaryl-β-diketone, for example one of those disclosed in U.S. Pat. No. 4,565,790 or European Patent 0,064,484. The present invention does, however, permit the use of other chelating chromophores. The chromophore can be added as a component of the solution lowering the pH or separately whilst the material is at low pH, but it may be more convenient, especially when the chromophore is sensitive to low pH or has poor solubility at low pH, to add the chromophore as a component of the solution raising the pH. Examples of other chelating chromophores forming fluorescent complexes with lanthanides or other metals are to be found in the literature, for example in the paper by G. Kallistratos entitled "Fluorescent properties of aromatic complexes with rare earths and other elements of the IIIa Group" in Chimika Chronika, New Series, 11,249-266 (1982), and such materials and their derivatives having strong fluorescent activity could be used in the present invention. Pyridoxamine, p-aminosalicylic acid, morin, hydroxykynurenine, dipicolinic acid, tiron and their analogues are examples of other chelating chromophores. The chelating chromophore may be contacted with the liberated metal ion whilst the chromophore is free in solution or immobilised on a solid substrate to which it has been attached by physical or chemical bonds. Conventional substrates or those disclosed in the literature may be used for this purpose.

The solution which lowers the pH and/or the solution which incorporates the chromophore can also include a detergent, for example TRITON X-100 or other compound reducing surface tension, to assist in solubilising the chromophore, especially when using a β-diketone as chromophore. Likewise a Lewis base such as a phosphine or phosphine oxide, for example trioctylphosphine oxide (TOPO), can be included in the pH-lowering solution or the pH-increasing solution to increase the stability of the chelate, especially in the case of β-diketones. However, the presence of these two ingredients is not essential and they may be omitted, especially when using other chelating chromophores such as tiron, dipicolinic acid and their analogues.

The lanthanide metal used may be any of those known to be suitable, for example Eu$^{3+}$ and Tb$^{3+}$, and the chelating agent used to form the initial chelate with the biological substance and the lanthanide metal ion may likewise be any of those known or described in the literature for the purpose, for example EDTA and its analogues, polycarboxylic acids or other protonisable compounds being preferred.

Examples of other metals, with corresponding suitable chromophores, are given in the above-mentioned paper by G. Kallistratos. Most transition elements form coloured products with a wide variety of compounds. For example Mn, Fe, Co, Ni, Cu and Zn form coloured products with chromophores such as derivatives of pyridine. The colour usually is determined by the state of oxidation of the metal ion. The use of these other metals may be of especial value where there are constraints on instrumentation or high sensitivity might not be required.

The fluorescence spectroscopy, luminometry (chemiluminescence) or colourometry may, with the exception of the features mentioned above, be conducted in any known or conventional manner or manner described in the literature. Procedures for these techniques are, for example, mentioned or discussed in "Alternative Immunoassays", edited W. P. Collins, John Wiley & Sons Ltd. (1985) and "Practical Immunoassay", edited W. Butt, Marcel Dekker Inc. (1984) and in the references listed there, also in "Ligand-Binder Assays: Labels and Analytical Strategies", by L. J. Kricka, Marcel Dekker Inc. (1985), especially chapters 5 and 8. It will be appreciated that all necessary steps should be taken in the present invention to ensure that the metal ion amount actually determined is representative of the biological substance to be determined, including removal of any excess of the metal ion prior to dissociation of the complex with the biological substance, the use of standard or accurately known amounts where necessary and the preparation of standard curves for calibration purposes as appropriate.

The invention may be used for the determination of biological substances normally present in small quantities, for example substances of any of the types mentioned in our International Patent Application published as WO86/01604, namely antigens, antibodies, hormones, enzymes, other proteins and haptens and other substances naturally occurring in human or animal body fluids or cultivated or generated artificially. The present invention may be used in conjunction with the invention disclosed in that application to provide an advantageous overall procedure, and the contents of that application are incorporated herein by this reference. It may be used in conjunction with labelled antibodies, antigens or DNA fragments.

EXAMPLES AND BRIEF DESCRIPTION OF THE DRAWINGS

The invention is further illustrated by graphs forming the accompanying drawings In the drawings, FIG. 1 shows graphically the relationship between optimum chromophore concentration and enhancement pH in an assay of IgG.

FIG. 6 shows a calibration curve in an AFP assay obtained under similar conditions to those in FIG. 5.

Figure 1:
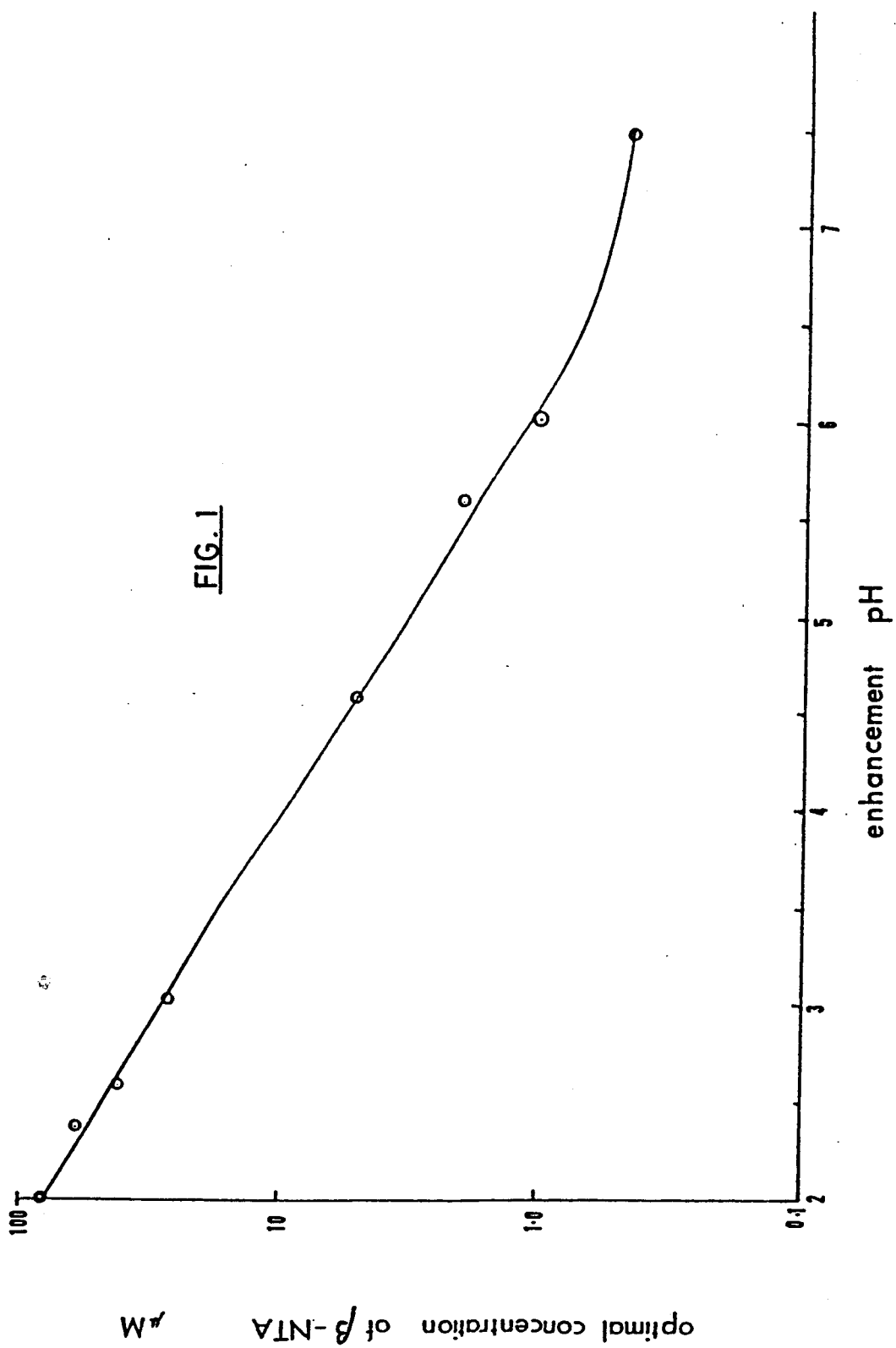

Referring to FIG. 1, an assay of rabbit IgG was performed using $Eu^{3+}$ and phenyl-EDTA as chelating agent, and the pH of the initial complex was reduced to 1.7 by the addition of a small amount of strong acid (HCl). The pH was then raised again in the presence of an enhancement solution (β2-diketone such as NTA+-TOPO+TRITON×100) by means of tris/HCl buffer or tris/acetate buffer to a value of from 3 to 8 prior to measurement of the fluorescence in a conventional manner. At each pH the optimal amount of β-diketone was used and it was found that the amount of β-diketone needed for optimal results decreased with increasing pH, as shown in FIG. 1.

Figure 2:
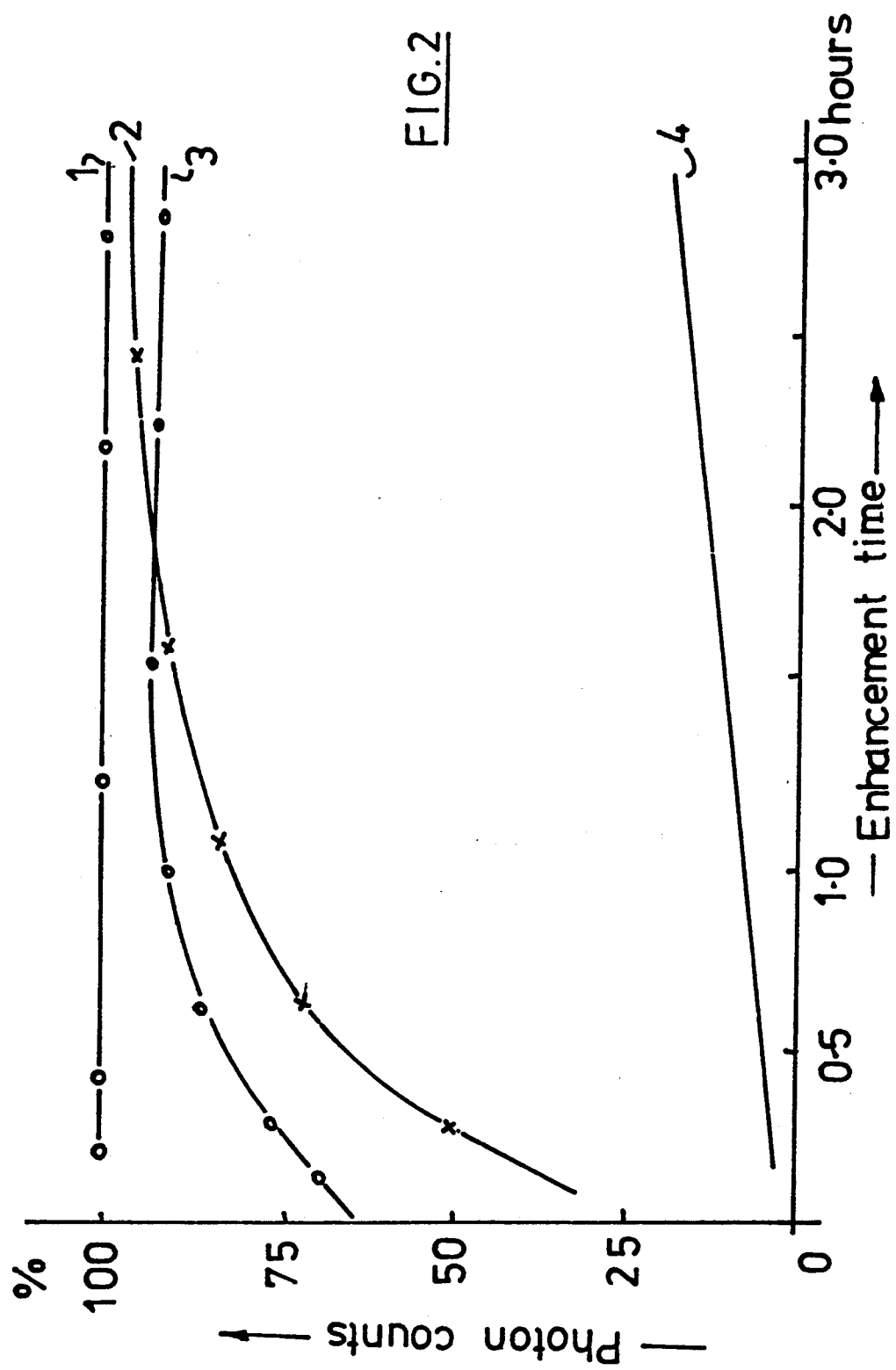
FIG. 2 shows a comparison of the kinetics and efficiency of enhancement by the two-step and single step methods for enhancement using β-NTA (2-naphthoyltrifluoroacetone) as chelating chromophore from a Eu(III) - EDTA-antibody initial chelate.
Figure 3:
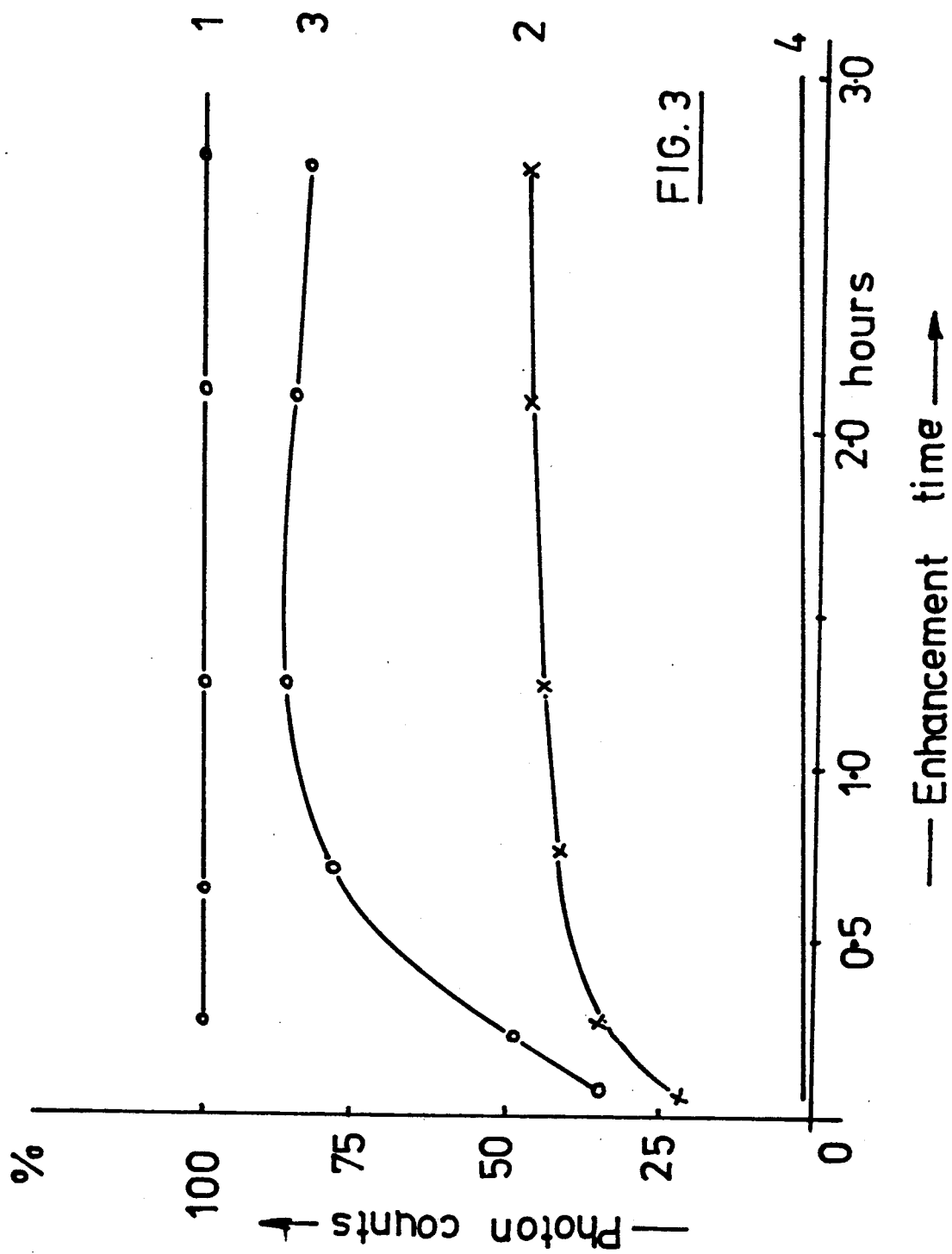
FIG. 3 shows a similar comparison using the same β-diketone but starting from a Eu(III) DTPA-antibody initial chelate.
Figure 4:
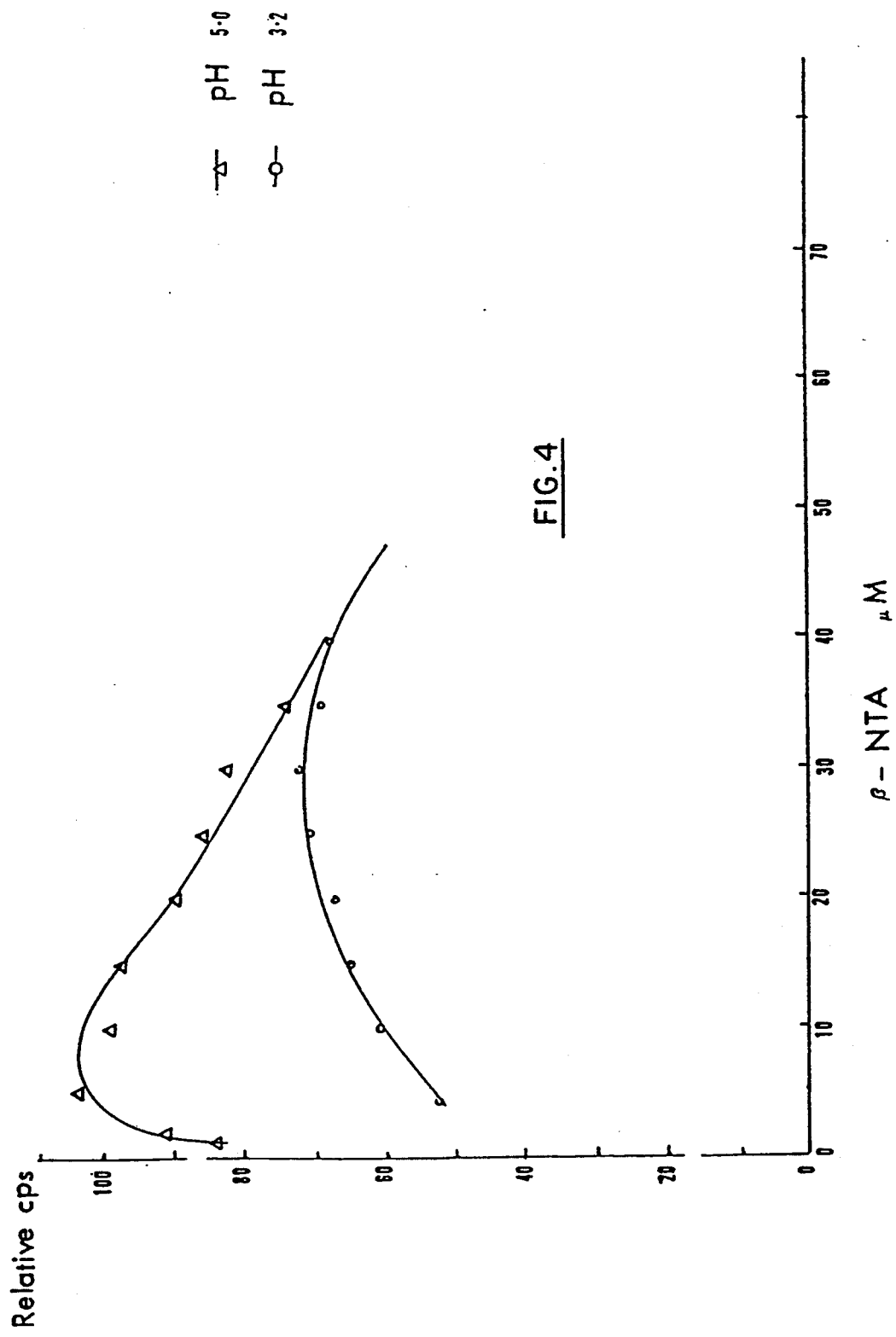
FIG. 4 shows the effect of β-diketone concentration on fluorescence counts at pH 5.0, which is optimal, and pH 3.2, which facilitates rapid one-step enhancements.

In FIGS. 2 and 3 line 4 shows the results obtained at pH 7.6, as required for optimal photon yield with dipicolinic acid; line 3 shows the results obtained at pH 3.2, revealing rapid enhancement and acceptable photon yield; line 2 shows the results achieved with single-step enhancement at pH 5.0, the pH of optimal photon yield by β-NTA; and line 1 shows the results achieved with two-step enhancement at pH 1.7 followed by 5.0. In both cases line 1 is the best.

Separate experimental work on measurement of photon counts from Eu(III) at $10^{-8}$M concentration in β-NTA enhancement solution using optimal β-NTA concentration at various pHs and 100 μM TOPO has shown a maximum photon count at pH 5.0 (146930) the count remaining at or above 125000 over the pH range 4.5–7.0 but dropping sharply outside that range, being only 101581 at pH 3.2 and 92000 at pH 7.7.

Figure 5:
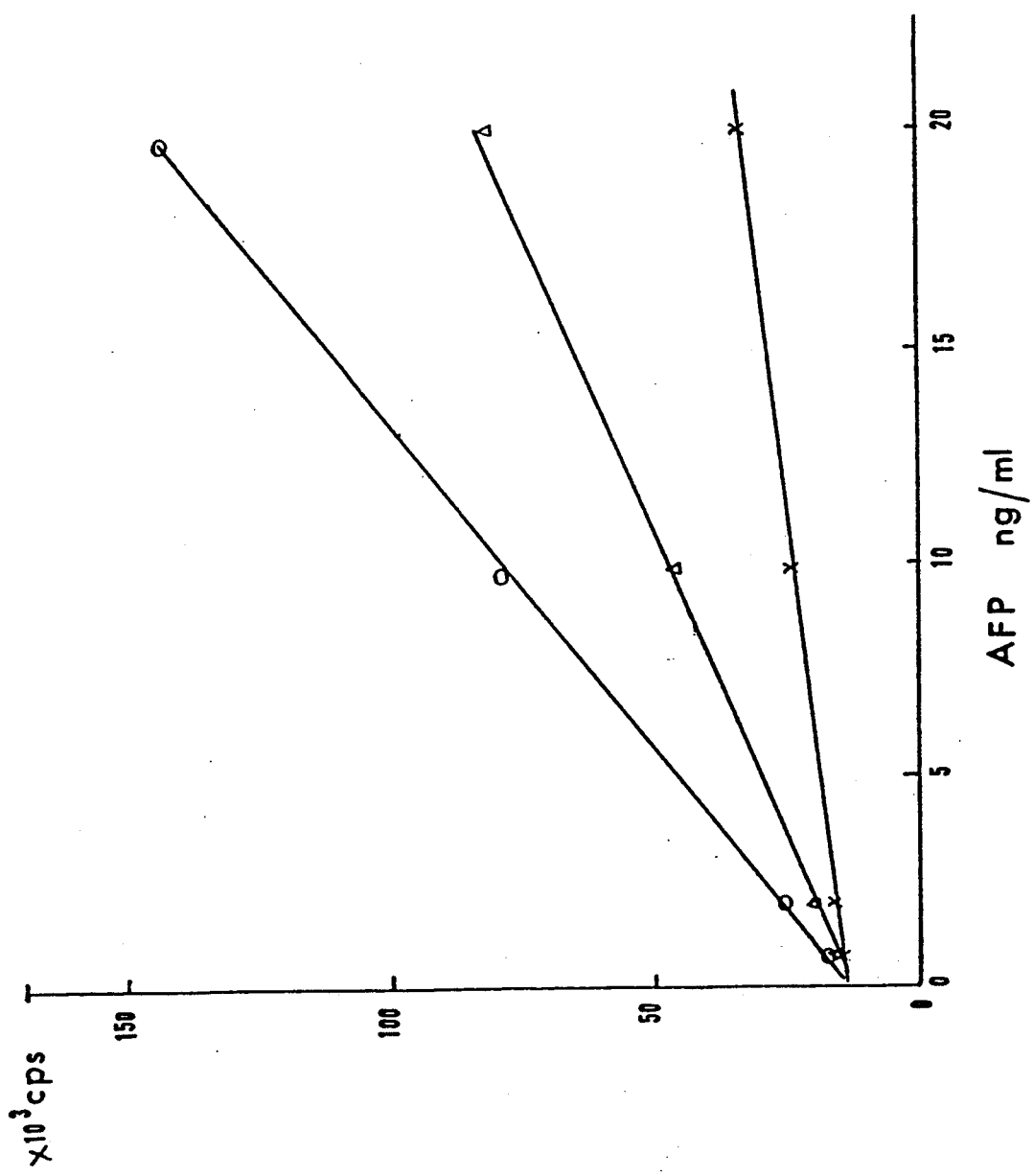
FIG. 5 shows calibration curves in three identical two-site assays.

Referring to FIG. 5, the assays involved AFP which was estimated with the aid of rabbit anti-AFP coated on a polystyrene tube as a first antibody rabbit anti-AFP conjugated with diethylene triamine pentaacetic acid (DTPA) using a p-nitrophenyl mono-active ester of DTPA and chelated with Eu(III) as a second antibody. Europium fluorescence was enhanced with β-diketone-TOPO solution in three ways, namely:

(i) two-step enhancement at pH 5.0 (300 =1 of 0.02M HCl for 5 minutes followed by 300 μl of 12μM β-NTA for 5 minutes);

(ii) one-step enhancement at pH 5.0 (600 μl of 6 μM β-NTA for 30 minutes); and (iii) one-step enhancement at pH 3.0 (600 μl of 25,μM β-NTA)

The final solutions each had 200 μM TOPO and 0.1% TRITON×100.

The assay concerned in FIG. 6 was also an AFP assay but it differed from that reported upon in FIG. 5 by using Tb(III) as metal ion instead of Eu(III) and by using two-step enhancement at pH 13 with 40 μM tiron (final concentration 20 μM).

I claim:

1. A process for the determination of a biological substance, comprising the steps of:

(1) providing the biological substance with a bound marker comprising a chelate complex composed of
  (i) a lanthanide metal ion capable of being detected in conjunction with a chelating chromophore, and
  (ii) a first chelate-forming compound capable of coupling the lanthanide metal ion to the biological substance, (2) freeing the biological substance with bound chelate complex from measurement-interfering contents of the metal ion, (3) dissociating the chelate complex bound to the biological substance by reduction of the pH to between 1.5–3.0 without the incorporation of a detergent for the dissociation, so as to liberate the metal ion; and (3) determining the quantity of metal ion liberating from the chelate complex bound to the biological substance, as a measure of the amount of the biological substance present, following formation of a different chelate complex between the liberated metal ion and a second chelate-forming compound capable of operating as a chelating chromophore for the metal ion, the determination of the quantity of metal ion liberated from said chelate complex bound to the biological substance being carried out at a pH above 3.5 up to 12.

2. A process as claimed in claim 1, wherein the pH is reduced to a pH from 2.0 to 3.0 for dissociation.

3. A process as claimed in claim 1, wherein the quantity of metal ion liberated from the chelate complex bound to the biological substance is determined by fluorescence spectroscopy, luminometry or colourometry.

4. A process as claimed in claim 1, wherein the high pH is achieved by means of a buffer.

5. A process as claimed in claim 1, wherein the chelating chromophore is a beta-diketone.

6. A process as claimed in claim 5, wherein the beta-diketone is incorporated after reduction of the pH level.

7. A process as claimed in claim 1, wherein the chelating chromophore is dipicolinic acid, pyridoxamine, p-aminosalicyclic acid, morin, hydroxykynurenine, 4,5-dihydroxy-1,3-benzenedisulfonic acid, and the salts thereof.

8. A process as claimed in claim 1, wherein the europium or terbium ions are used as the metal ion.

9. A process as claimed in claim 1, wherein the liberated metal ion and the chelating chromophore are brought into contact, for formation of the complex between them and determination of the metal ion, whilst the chelating chromophore is physically or chemically immobilized with the aid of a solid substrate.

10. A process as claimed in claim 1, wherein the determination of the metal ion is carried out by a time-resolved signal methodology.

11. A process as claimed in claim 1, wherein the determination of the metal ion is completed within about 10 minutes after the initial reduction of the pH for liberation of metal ion from the chelate complex bound to the biological substance.

12. A process for the fluorescence spectroscopic determination of a biological substance provided with a marker consisting of a lanthanide chelate complex formed of a lanthanide metal ion coupled to the biological substance via a chelate-forming compound, which method includes the step of adding to the chelate complex bound to the biological substance a solution which reduces the pH to 1.5–3.0 at which the lanthanide metal ion becomes dissociated from the chelate complex, prior to determination of the lanthanide metal ion as a complex with a chelating chromophore different from the chelate-forming compound; the determination of the lanthanide metal ion as a complex with the different chelating chromophore being carried out at pH above 4.0 up to 12, above pH 3.5 and closer to its fluorescence peak for optimum sensitivity.

13. A process as claimed in claim 12, wherein the pH is increased by addition of a further solution.

14. A process as claimed in claim 13, wherein the further solution contains the different chelating chromophore.

15. A process as claimed in claim 12, wherein the high pH is achieved by means of a buffer.

16. A process as claimed in claim 12, wherein the chelating chromophore is a beta-diketone.

17. A process as claimed in claim 16, wherein the beta-diketone is incorporated after reduction of the pH level.

18. A process as claimed in claim 12, wherein the chelating chromophore is dipicolinic acid, pyridoxamine, p-aminosalicyclic acid, morin, hydroxykynurenine, 4,5-dihydroxy-1,3-benzenedisulfonic acid, and the salts thereof.

19. A process as claimed in claim 16, wherein no detergent is incorporated during the process.

20. A process as claimed in claim 16, wherein the europium or terbium ions are used as the metal ion.

21. A process as claimed in claim 12, wherein the liberated metal ion and the chelating chromophore are brought into contact, for formation of the complex between them and determination of the metal ion, whilst the chelating chromophore is physically or chemically immobilized with the aid of a solid substrate.

22. A process as claimed in claim 12, wherein the determination of the metal ion is carried out by a time-resolved signal methodology.

23. A process as claimed in claim 12, wherein the determination of the metal ion is completed within about 10 minutes after the initial reduction of the pH for liberation of metal ion from the chelate complex bound to the biological substance.

* * * * *

UNITED STATES PATENT AND TRADEMARK OFFICE
CERTIFICATE OF CORRECTION

PATENT NO. : 5,124,268

DATED : June 23, 1992

INVENTOR(S) : S. Dakubu

It is certified that error appears in the above-identified patent and that said Letters Patent is hereby corrected as shown below:

Column 6, line 6, delete "62" and insert --$\beta$--.

Column 6, line 33, before "rabbit" insert --,--.

Column 6, line 39, delte "=" and insert --$\mu$--.

Column 6, line 44, after "25" delete --,--.

Column 7, line 21, delete "high" and insert --higher--.

Column 7, line 28, after "chromophore is" insert --selected from the group consisting of--.

Column 8, line 5, after "pH to" insert --between--.

Column 8, line 27, after "chromophore is" insert --selected from the group consisting of--.

Column 8, line 34, delete "the".

Signed and Sealed this

Twelfth Day of October, 1993

Attest:

BRUCE LEHMAN

*Attesting Officer*     Commissioner of Patents and Trademarks